(12) United States Patent
Burbank et al.

(10) Patent No.: US 7,594,890 B2
(45) Date of Patent: *Sep. 29, 2009

(54) MULTI-AXIAL UTERINE ARTERY IDENTIFICATION, CHARACTERIZATION, AND OCCLUSION DEVICES

(75) Inventors: Fred Burbank, Laguna Niguel, CA (US); Greig E. Altieri, Laguna Beach, CA (US); Michael L. Jones, San Clemente, CA (US)

(73) Assignee: Vascular Control System, Inc., San Jaun Capistrano, CA (US)

( * ) Notice: Subject to any disclaimer, the term of this patent is extended or adjusted under 35 U.S.C. 154(b) by 461 days.

This patent is subject to a terminal disclaimer.

(21) Appl. No.: 10/107,800

(22) Filed: Mar. 28, 2002

(65) Prior Publication Data

US 2002/0165579 A1    Nov. 7, 2002

Related U.S. Application Data

(60) Provisional application No. 60/279,477, filed on Mar. 28, 2001.

(51) Int. Cl.
*A61B 8/06* (2006.01)

(52) U.S. Cl. .................. 600/453; 600/439; 600/454; 600/504; 606/119; 606/158; 606/205

(58) Field of Classification Search .......... 600/439, 600/454, 504, 453; 606/205, 119, 158
See application file for complete search history.

(56) References Cited

U.S. PATENT DOCUMENTS

| | | | | |
|---|---|---|---|---|
| 105,901 | A | * | 8/1870 | unkn .................. 294/99.2 |
| 319,954 | A | * | 6/1885 | unkn .................. 294/99.2 |
| 1,715,089 | A | * | 5/1929 | Jones .................. 81/64 |
| 1,789,524 | A | * | 1/1931 | Hall .................. 294/99.2 |
| 1,806,441 | A | * | 5/1931 | Bauer et al. .................. 294/99.2 |
| 2,400,251 | A | | 5/1946 | Nagel |
| 2,522,293 | A | * | 9/1950 | Noble .................. 366/14 |
| 2,723,666 | A | * | 11/1955 | Greenberg .................. 606/1 |
| 3,063,455 | A | | 11/1962 | Markley |
| 3,411,505 | A | | 11/1968 | Nobis |
| 3,777,740 | A | | 12/1973 | Hokanson |

(Continued)

FOREIGN PATENT DOCUMENTS

DE    195 28 440 A    2/1997

(Continued)

OTHER PUBLICATIONS

International Preliminary Report of Patentability for Serial No. PCT/US04/01935, mailed Jul. 8, 2005.

(Continued)

*Primary Examiner*—Brian Casler
*Assistant Examiner*—Jonathan G Cwern

(57) ABSTRACT

A system is provided for compressing one or both of the uterine arteries of a patient which is at least in part shaped to complement the shape of the exterior of the cervix, which allows the system to be self-positioning. One or more Doppler chips can be mounted or incorporated into the system which permit the practitioner to better identify the uterine artery and monitor blood flow therein. A tenaculum-like element can be further included which secures the system to the patient's cervix.

36 Claims, 8 Drawing Sheets

U.S. PATENT DOCUMENTS

| | | | |
|---|---|---|---|
| 3,779,248 A | | 12/1973 | Karman |
| 4,073,533 A | * | 2/1978 | De brey et al. ............... 294/118 |
| 4,120,302 A | | 10/1978 | Ziegler |
| 4,192,313 A | | 3/1980 | Ogami |
| 4,206,750 A | * | 6/1980 | Kaivola ....................... 600/220 |
| 4,226,240 A | | 10/1980 | Walker, Jr. |
| 4,292,960 A | | 10/1981 | Paglione |
| 4,428,374 A | | 1/1984 | Auburn |
| 4,428,379 A | | 1/1984 | Robbins et al. |
| 4,475,544 A | | 10/1984 | Reis |
| 4,509,528 A | | 4/1985 | Sahota |
| 4,589,419 A | | 5/1986 | Laughlin et al. |
| 4,650,466 A | | 3/1987 | Luther |
| 4,757,823 A | | 7/1988 | Hofmeister et al. |
| 4,768,288 A | * | 9/1988 | Culbertson ................... 30/142 |
| 4,771,788 A | | 9/1988 | Millar |
| 4,945,896 A | * | 8/1990 | Gade ........................... 600/202 |
| 4,994,069 A | | 2/1991 | Ritchart et al. |
| 5,037,430 A | | 8/1991 | Hasson |
| 5,081,997 A | | 1/1992 | Bosley, Jr. et al. |
| 5,108,408 A | | 4/1992 | Lally |
| 5,201,314 A | | 4/1993 | Bosley et al. |
| 5,226,911 A | | 7/1993 | Chee et al. |
| 5,275,166 A | * | 1/1994 | Vaitekunas et al. .......... 600/439 |
| 5,289,831 A | | 3/1994 | Bosley |
| 5,336,231 A | | 8/1994 | Adair |
| 5,383,922 A | | 1/1995 | Zipes et al. |
| 5,427,108 A | | 6/1995 | Bollinger |
| 5,447,351 A | * | 9/1995 | Klunder ....................... 294/99.2 |
| 5,447,515 A | | 9/1995 | Robicsek |
| 5,456,693 A | | 10/1995 | Conston et al. |
| 5,458,596 A | | 10/1995 | Lax et al. |
| 5,488,958 A | | 2/1996 | Topel et al. |
| 5,507,744 A | | 4/1996 | Tay et al. |
| 5,520,698 A | | 5/1996 | Koh |
| 5,542,944 A | | 8/1996 | Bhatta |
| 5,549,624 A | | 8/1996 | Mirigian et al. |
| 5,549,824 A | | 8/1996 | Trumpf et al. |
| 5,556,396 A | | 9/1996 | Cohen et al. |
| 5,588,960 A | | 12/1996 | Edwards et al. |
| 5,591,173 A | | 1/1997 | Schifano |
| 5,598,841 A | | 2/1997 | Taniji et al. |
| 5,601,323 A | * | 2/1997 | Kaiser ........................... 294/7 |
| 5,614,204 A | | 3/1997 | Cochrum |
| 5,662,676 A | | 9/1997 | Koninckx |
| 5,662,680 A | | 9/1997 | Desai |
| 5,672,153 A | | 9/1997 | Lax et al. |
| 5,674,243 A | | 10/1997 | Hale |
| 5,691,314 A | | 11/1997 | Hodgen |
| 5,697,942 A | | 12/1997 | Palti |
| 5,713,371 A | * | 2/1998 | Sherman et al. ............. 600/436 |
| 5,713,896 A | | 2/1998 | Nardelia |
| 5,713,942 A | | 2/1998 | Stern et al. |
| 5,715,832 A | | 2/1998 | Koblish et al. |
| 5,716,389 A | | 2/1998 | Walinsky et al. |
| 5,720,743 A | | 2/1998 | Bischof et al. |
| 5,759,154 A | | 6/1998 | Hoyns |
| 5,766,135 A | | 6/1998 | Terwilliger |
| 5,776,129 A | | 7/1998 | Mersch |
| 5,792,059 A | * | 8/1998 | Furia et al. ................... 600/459 |
| 5,797,397 A | | 8/1998 | Rosenberg |
| 5,800,378 A | | 9/1998 | Edwards et al. |
| 5,817,022 A | | 10/1998 | Vesely |
| 5,836,906 A | | 11/1998 | Edwards |
| 5,840,033 A | | 11/1998 | Takeuchi |
| 5,895,386 A | | 4/1999 | Odell et al. |
| 5,899,861 A | | 5/1999 | Friemel et al. |
| 5,910,484 A | | 6/1999 | Haupert, Jr. |
| 5,911,691 A | | 6/1999 | Mochizuki et al. |
| 5,916,173 A | * | 6/1999 | Kirsner ....................... 600/551 |
| 5,921,933 A | | 7/1999 | Sarkis et al. |
| 5,922,008 A | | 7/1999 | Gimpelson |
| 5,941,889 A | | 8/1999 | Cermak |
| 5,979,453 A | | 11/1999 | Savage et al. ............... 128/898 |
| 6,013,088 A | | 1/2000 | Karavidas |
| 6,015,541 A | | 1/2000 | Greff et al. |
| 6,019,724 A | | 2/2000 | Gronningsaeter et al. |
| 6,032,673 A | | 3/2000 | Savage et al. ............... 128/898 |
| 6,033,398 A | | 3/2000 | Farley et al. |
| 6,034,477 A | | 3/2000 | Peeters et al. |
| 6,035,238 A | | 3/2000 | Ingle et al. |
| 6,045,508 A | | 4/2000 | Hossack et al. |
| 6,066,139 A | | 5/2000 | Ryan et al. |
| 6,077,257 A | | 6/2000 | Edwards et al. |
| 6,080,118 A | * | 6/2000 | Blythe ........................ 600/591 |
| 6,106,473 A | | 8/2000 | Violante et al. |
| 6,152,874 A | | 11/2000 | Looney et al. |
| 6,169,914 B1 | * | 1/2001 | Hovland et al. ............. 600/340 |
| 6,175,751 B1 | * | 1/2001 | Maizes ....................... 600/338 |
| 6,210,330 B1 | * | 4/2001 | Tepper ....................... 600/439 |
| 6,231,515 B1 | | 5/2001 | Moore et al. |
| 6,254,601 B1 | * | 7/2001 | Burbank et al. ............... 606/45 |
| 6,261,234 B1 | * | 7/2001 | Lin ............................ 600/461 |
| 6,280,441 B1 | | 8/2001 | Ryan |
| 6,293,954 B1 | | 9/2001 | Fogarty et al. |
| 6,299,621 B1 | | 10/2001 | Fogarty et al. |
| 6,494,517 B1 | * | 12/2002 | Durant ....................... 294/99.2 |
| 6,602,251 B2 | * | 8/2003 | Burbank et al. ............... 606/45 |
| 6,610,074 B2 | | 8/2003 | Santilli |
| 6,764,488 B1 | * | 7/2004 | Burbank et al. ............... 606/51 |
| 6,905,506 B2 | * | 6/2005 | Burbank et al. ............. 606/205 |
| 7,141,057 B2 | * | 11/2006 | Burbank et al. ............. 606/148 |
| 7,172,603 B2 | * | 2/2007 | Burbank et al. ............. 606/119 |
| 7,207,996 B2 | * | 4/2007 | Burbank et al. ............. 606/151 |
| 7,223,279 B2 | * | 5/2007 | Burbank et al. ............. 606/205 |
| 7,229,465 B2 | * | 6/2007 | Burbank et al. ............. 606/205 |
| 7,329,265 B2 | * | 2/2008 | Burbank et al. ............. 606/157 |
| 7,354,444 B2 | * | 4/2008 | Burbank et al. ............. 606/157 |
| 7,404,821 B2 | * | 7/2008 | Burbank et al. ............. 606/205 |
| 2002/0111537 A1 | | 8/2002 | Taylor et al. |
| 2002/0165579 A1 | | 11/2002 | Burbank et al. |
| 2002/0183771 A1 | | 12/2002 | Burbank et al. |
| 2002/0188306 A1 | | 12/2002 | Burbank et al. |
| 2003/0018270 A1 | | 1/2003 | Makin et al. |
| 2003/0120306 A1 | | 6/2003 | Burbank et al. |
| 2004/0097962 A1 | | 5/2004 | Burbank et al. |
| 2004/0153097 A1 | | 8/2004 | Burbank et al. |
| 2005/0113634 A1 | | 5/2005 | Burbank et al. |
| 2005/0113852 A1 | | 5/2005 | Burbank et al. |

FOREIGN PATENT DOCUMENTS

| | | |
|---|---|---|
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 | 1/1997 |
| GB | 2 311 468 A | 1/1997 |
| JP | 63-46105 | 3/1988 |
| JP | 1159821 | 11/1989 |
| JP | 7-008493 A | 1/1995 |
| WO | WO 95/02370 | 1/1995 |
| WO | WO 95/02371 | 1/1995 |
| WO | WO 98/19713 | 5/1998 |
| WO | WO 98/38486 A | 9/1998 |
| WO | WO 99/11179 A | 3/1999 |
| WO | WO 00/33724 A | 6/2000 |
| WO | WO 01/68720 | 9/2001 |
| WO | WO 01/80713 | 11/2001 |
| WO | WO 02/00192 | 1/2002 |
| WO | WO 02/78521 | 10/2002 |
| WO | WO 02/078522 A2 | 10/2002 |
| WO | WO 2004/045420 A2 | 6/2004 |

| | | | |
|---|---|---|---|
| WO | WO 2004/045426 A1 | 6/2004 | |
| WO | WO 2004/071275 A2 | 8/2004 | |

OTHER PUBLICATIONS

International Search Report for PCT/US2004/038111, mailed May 3, 2005.
Written Opinion for PCT/US2004/038111, mailed May 3, 2005.
Translation of FR 1 220 773.
International Search Report for PCT/US2004/038276, mailed Mar. 15, 2005.
International Search Report for PCT/US04/03023 mailed Feb. 9, 2005.
International Search Report for PCT/US03/35815 mailed Jun. 30, 2004.
International Search Report for PCT/US02/09549, mailed Jun. 30, 2003.
International Search Report for PCT/US02/09775, mailed Sep. 12, 2002.
Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.
Brohim, Robert M. et al., "Development of Independent Vessel Security After Ligation With Absorbable Sutures or Clips", *The American Journal of Surgery*, Mar. 1993, vol. 165, pp. 345-348.
Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.
Hay, D.L. et al., "Hemostasis in Blood Vessels After Ligation", *Am. J. Obstet Gynecol*, Mar. 1989, 160:3, pp. 737-739.
Hunerbein, M. et al., "Endoscopic Ultrasound-Guided Real Time Biopsy of Peri-Intestinal Tumors", *Surgical Technology International VII*, 1998, pp. 91-95.
O'Leary, James A., M.D., "Uterine Artery Ligation in the Control of Postcesarean Hemorrhage", *The Journal of Reproductive Medicine, Inc.*, 40(3):189-193 (Mar. 1995).
Schaefer, C.J. et al., "Absorbable Ligating Clips", *Surg. Gynecol. Obstet.*, 1982, 154:513-516.
"Mick 200-TP Applicator Package", Mick Radio-Nuclear Instruments, Inc., advertisement.
"Multiplanar Biopsy Transverse Scan", Bruel & Kjaer Medical Systems, Inc., advertisement.
"Seeding Device—Proscan Urologic Ultrasound Imaging System", Teknar, advertisement.
Sonopsy Ultrasound Guided Breast Biopsy, NeoVision, advertisement.
"Transrectal Biopsy of the Prostrate Gland", Bruel & Kjaer Medical Systems, Inc., advertisement.
International Search Report for PCT/US2006/031226 mailed Dec. 6, 2006.
Written Opinion of the International Searching Authority for PCT/US2006/031226 mailed Dec. 6, 2006.
International Preliminary Report on Patentability and Written Opinion of the International Searching Authority for International Application No. PCT/US2006/031226, mailed Mar. 13, 2008.
Bateman, William M.D., "Treatment of intractable menorrhagia by bilateral uterine vessel, Interruption", *Am. J. Obst. & Gynec.* 89(6):825-827 (Jul. 15, 1964).
Brigato, G. et al., "A Noninvasive Instrumental Method in Severe Postpartum Hemorrhages", *Minerva ginecologica* 50(7-8):337-339 (1998).
Ravine, J. H. et al., "Arterial embolisation to treat uterine myomata", *The Lancet* 346:671-672 (Sep. 9, 1995).
Garza Leal, J. et al., "Myoma Treatment by Transient Uterine Ischemia" *The Journal of the American Assoication of Gynecologic Laparoscopists* 7(3):S31 (Aug. 2000).
Fuchs, Karl, "Afibrinogenemia Treated by Ligation of Uterine Arteries" *Gynacologic* 148:407-411(1959).
O'Leary, James A., M.D. "Uterine Artery Ligation in the Control of Postcesarean Hemorrhage" *Am. J. Obst. & Gynec.* 94(7):920-924 (Apr. 1, 1996).
O'Leary, James L., M.D. et al., "Uterine artery ligation in the control of intractable postpartum hemorrhage" *Am. J. Obst. & Gynec.* 94(7):920-924 (Apr. 1, 1966).

* cited by examiner

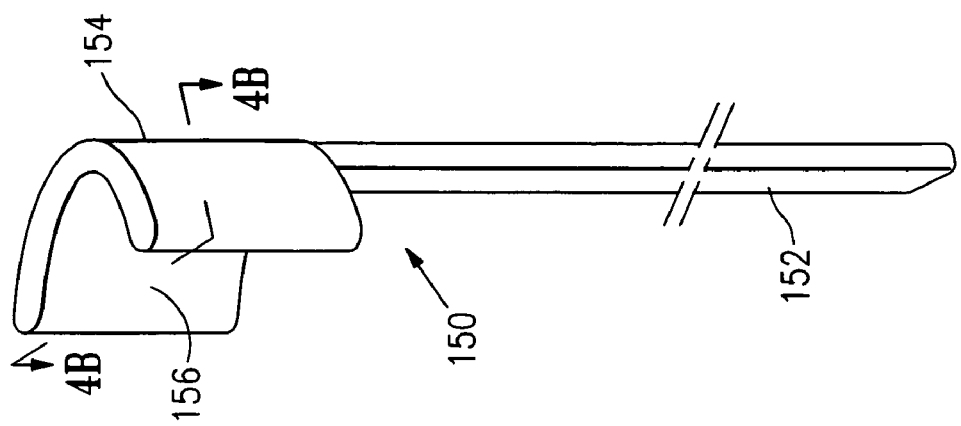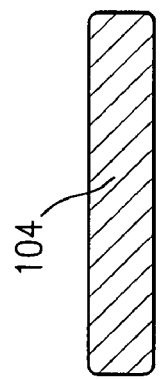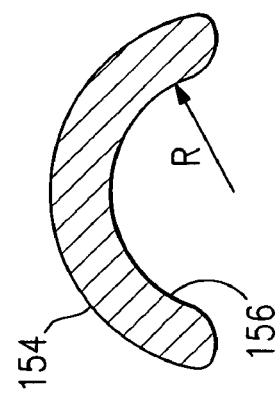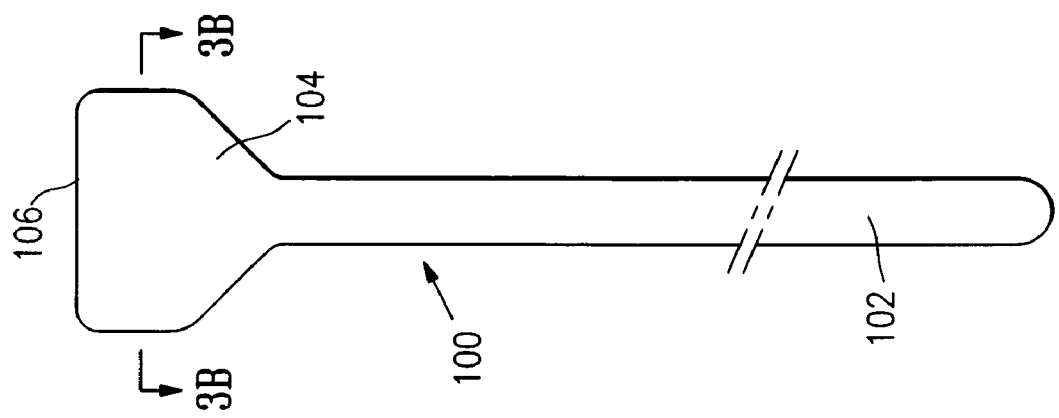

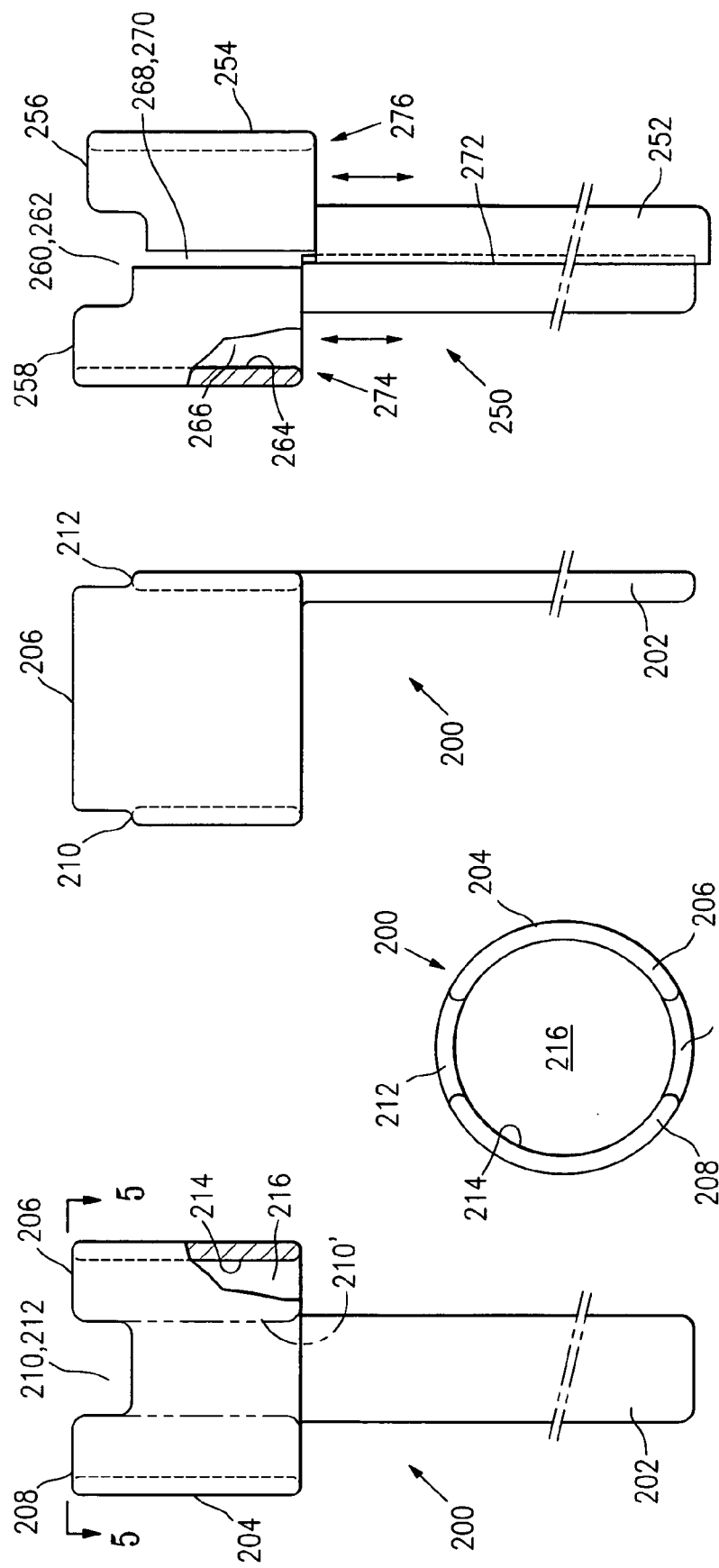

US 7,594,890 B2

MULTI-AXIAL UTERINE ARTERY IDENTIFICATION, CHARACTERIZATION, AND OCCLUSION DEVICES

This application is related and claims priority under 35 U.S.C. § 119 to U.S. provisional patent application Ser. No. 60/279,477, filed Mar. 28, 2001, the entire contents of which are incorporated by reference herein. This application is also related to an application filed on Mar. 28, 2002, entitled "Multi-axial uterine artery identification, characterization, and occlusion pivoting devices and methods", by Fred Burbank, Grieg E. Altieri, and Michael L. Jones, assigned U.S. application Ser. No. 10/107,810, now U.S. Pat. No. 6,905,506, the entire contents of which are incorporated by reference herein.

BACKGROUND OF THE INVENTION

1. Field of the Invention

The present invention relates to devices, systems, and processes useful for compressing a uterine artery, and more particularly to devices and systems capable of easily locating, compressing, and/or monitoring or characterizing the blood flow through a uterine artery.

2. Brief Description of the Related Art

It has been proposed that occlusion of the uterine arteries of a human female patient can kill myomata, i.e., fibroids, because of the relative frailty of the fibroids to anoxia or hypoxia, and the relatively high resistance of uterine tissues to anoxia or hypoxia. See Burbank, Fred, M.D., et al, Uterine Artery Occlusion by Embolization or Surgery for the Treatment of Fibroids: A Unifying Hypothesis-Transient Uterine Ischemia, The Journal of the American Association of Gynecologic Laparoscopists, November 2000, Vol. 7, No. 4 Supplement, pp. S3-S49. U.S. Pat. No. 6,254,601, to Fred Burbank et al, entitled "Methods for Occlusion of the Uterine Arteries", describes numerous devices and methods useful for occluding a uterine artery by penetrating the tissue of the patient to access the uterine artery. The devices and methods described in Burbank '601 have been useful in occluding a uterine artery, however there have been some difficulties encountered with their use.

Specifically, the aligned orientations of the imaging device, e.g., Doppler ultrasound device, and the element which passes through the tissue of the patient to occlude the uterine artery can be, for some patients and for some procedures, difficult to maintain. Additionally, the devices and methods described in the '601 patent do not necessarily take advantage of the structure and symmetry of the female human anatomy to facilitate occlusion of a uterine artery. The devices and methods of the '601 patent also are not well adapted for performing blood flow studies of a uterine artery.

Current devices available for uterine artery identification and characterization include two-dimensional Doppler color flow ultrasound systems with vaginal, abdominal, or intracavity probes. Typical machines are manufactured and distributed by General Electric Medical Systems, Toshiba, and Acuson, among other sources.

These machines require an ultrasound technologist to utilize the vaginal probe and position the probe sensor array within the vagina, near the cervix, while looking at the ultrasound machine's display screen, position the probe, and then select an appropriate setting to evaluate blood flow. Currently available devices thus require a high degree of skill to identify and then position the Doppler gate approximately to obtain an optimum signal for characterizing the blood flow. During this time, the probe must be held in as steady a position as possible to eliminate erroneous readings and signals. As will be readily appreciated by those of skill in the art, prior devices are therefore difficult to use successfully.

Current ultrasound machines can provide readings of peak blood velocity, pulsatility and resistive index, once a good Doppler wave form has been recorded. As discussed above, the trouble is in identification of the artery and, once identified, maintaining a good position for obtaining the desired data is difficult. No device which is currently commercially available can be used to simultaneously identify and occlude a uterine artery. Physicians, including gynecologists, have ligated the uterine artery surgically by using metal vascular clips or suture material, access having been achieved by surgical dissection. These surgical procedures have been performed by open abdominal surgery and laparoscopically, and require a great deal of surgical skill to access, identify, dissect, and ligate the uterine artery. This high skill requirement has limited the use of surgical ligation of the uterine arteries as a clinical alternative for treatment of uterine fibroids and other uterine disorders.

Ultrasound devices have been proposed for measuring blood flow in a blood vessel. See, e.g., U.S. Pat. Nos. 5,411,028, 5,453,575, 5,535,747, and 5,967,987.

Pessaries have been used for many years to treat numerous conditions, such as uterine prolapse, vaginal vault prolapse, urinary incontinence, cystocele, rectocele, enterocele, and some preoperative preparation. Pessaries have been available in numerous configurations, but are generally torus-shaped, somewhat elastic devices.

In an article published in 1964, Bateman reported that uterine artery vessel ligation or division, achieved via intraabdominal surgery similar to hysterectomy, was effective in treating menorrhagia both with and without myomectomy. Bateman, W., M.D., "Treatment of intractable menorrhagia by bilateral uterine vessel interruption", 89 Am. J. Obstet. Gynecol. 825-827 (Harcourt Health Sciences, Jul. 15, 1964). While Bateman reported some success, this procedure involves opening the abdominal cavity, with the known attendant risks and disadvantages.

There therefore remains a need in the art to develop apparatus and methods which further assist a medical practitioner in accessing, occluding, and/or measuring the blood flow characteristics in a uterine artery.

SUMMARY OF THE INVENTION

According to a first aspect of the invention, a device useful for compressing a uterine artery of a patient comprises a handle having a proximal end and a distal end, and a compressing portion mounted to the handle distal end, the compressing portion having a distal end face and a side surface.

According to another aspect of the present invention, a device useful for compressing a uterine artery of a patient comprises a handle having a proximal end and a distal end, and a cylindrical compressing portion mounted to the handle distal end, the compressing portion including a distal end having a distal end face, and including a hollow interior space sized to receive a cervix of a female human patient therein when the compressing portion is located around the cervix and the distal end face is positioned against the vaginal fornix of a female human patient.

According to yet another aspect of the present invention, a device useful for compressing a uterine artery of a patient comprises a compressing portion having a distal end face, a proximal end, and a side surface, a force transmission block on the compressing portion, and a grasping device attached to the force transmission block, the grasping device extending adjacent to the compressing portion.

According to yet another aspect of the present invention, a method of occluding a uterine artery of a female human patient, the patient having a uterus, a cervix with a cervical os, and a vaginal wall with a vaginal fornix, comprises pushing a compressing member upwardly toward the uterine artery until the compressing member reaches the vaginal fornix, pushing the compressing member upwardly to distend the vaginal wall at the vaginal fornix adjacent to the uterine artery, and pushing the uterine artery with the compressing member upwardly to compress the uterine artery against the uterus.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIGS. 3A and 3B illustrate side elevational and cross-sectional views, respectively, of a device according to one aspect of the present invention.

FIGS. 4A and 4B illustrate perspective and cross-sectional views, respectively, of a device according to another aspect of the present invention.

FIGS. 5A, 5B, and 5C illustrate three views of another embodiment in accordance with the present invention.

FIG. 6 illustrates a slidable embodiment of a device in accordance with the present invention.

DESCRIPTION OF THE PREFERRED EMBODIMENTS

Figure 1:
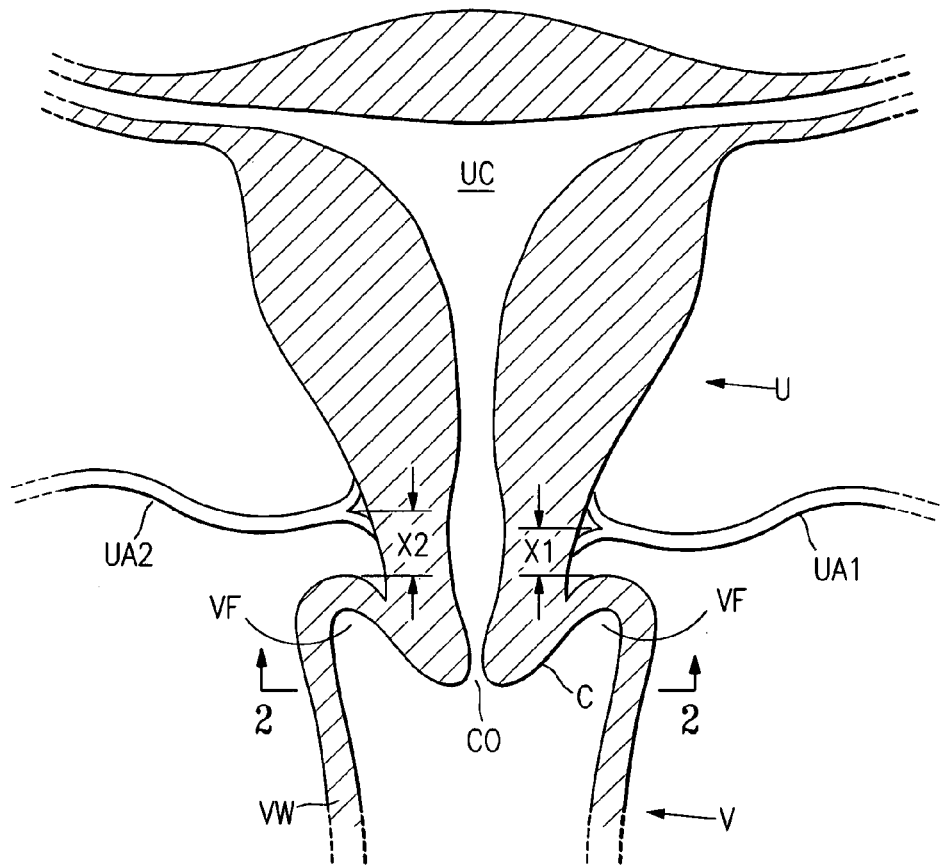
FIG. 1 illustrates simplified cross-sectional view of a uterus, cervix, and vagina of a female human in a coronal plane.

Referring to the drawing figures, like reference numerals designate identical or corresponding elements throughout the several figures.

The inventors herein have discovered that the uterine arteries of female humans typically are about 3 cm or less from the vaginal wall at the vaginal fornix where the uterine artery meets the uterus, although the uterine arteries for a single patient sometimes are spaced at slightly different distances (see distances X1 and X2 in FIG. 1). The inventors herein have also discovered that the right uterine artery is typically positioned between about the 1 and 5 o'clock (see FIG. 2) positions, and more frequently between about 2 and 4 o'clock; and that there is typically symmetry between the uterine arteries, i.e., that the left uterine artery is typically positioned between about the 7 and 11 o'clock positions, and more frequently between about 8 and 10 o'clock. The inventors herein have also discovered that the cervix can be used as a platform and a landmark from which to locate and access a uterine artery because of the axial symmetry of the cervix and it's generally cylindrical or frustoconical exterior shape. Furthermore, the inventors herein have discovered that the uterus, because it is a muscular and generally firm mass which resists deformation more than its adjacent tissues, including the uterine arteries, can be used as a backstop or anvil against which a uterine artery can be compressed. See also U.S. application Ser. No. 09/908,815, filed Jul. 20, 2001, to Fred Burbank et al. ("'815 application"),U.S. Pat No 7,223,279, co-assigned with the present application, for additional discussions of the anatomy of the uterus, cervix, and vaginal wall, the entire contents of which are incorporated by reference herein.

Devices and methods of the present invention can simplify the process of identifying a uterine artery and permits simultaneous interrogation and gathering of blood flow data for the artery. The device can be held in place and either selectively or automatically identifies the artery location and characteristics of the left and/or right side uterine artery without the need to reposition the Doppler array. Errors generated from positioning and repositioning the device in situ, and differences in the amount of pressure applied to the uterine artery for identification and interrogation, can successfully be lowered or eliminated. Devices according to the present invention permit simultaneous identification and occlusion of a uterine artery in a non-invasive manner, and lowers the level of skill needed to identify and occlude the artery because the devices and methods do not require surgical intervention to perform the occlusion.

Figure 2:
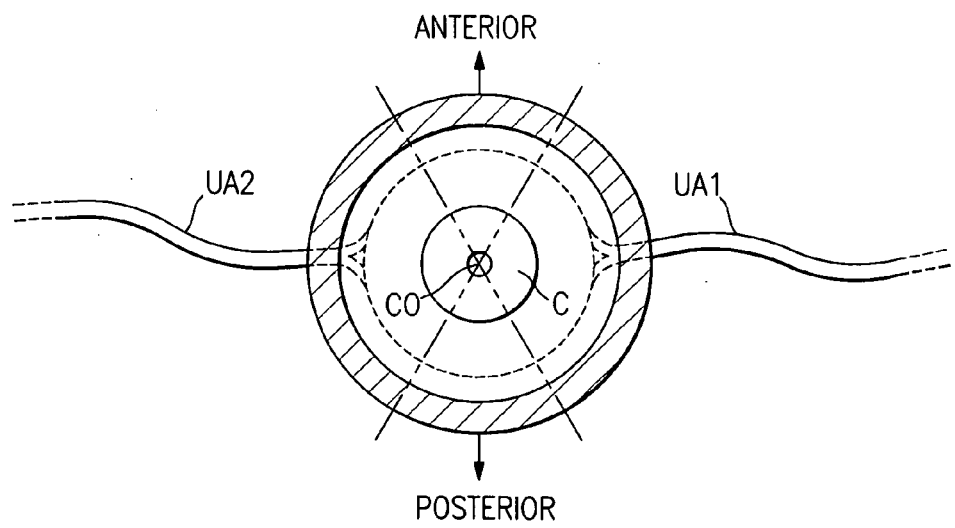
FIG. 2 illustrates a plan view taken at line 2-2 in FIG. 1 along an axial or transverse plane.

FIGS. 1 and 2 illustrate two different views of the uterus, cervix, vagina, and uterine arteries of a female human patient. Because reference will be made throughout this description to some of these anatomical structures, a brief discussion of this portion of the female human anatomy may prove useful. A uterus U includes a uterine cavity UC. The vagina V has a vaginal wall VW which extends upward to the vaginal fornix VF. The cervix C is (typically) centrally located and extends from the uterus U to a point typically somewhat below the vaginal fornix VF, and includes a cervical os CO which leads to the uterine cavity UC. Uterine arteries UA1 and UA2 lead to the uterus U from the inferior iliac artery (not illustrated). In this following descriptions, the orientations of the uterine arteries UA1 and UA2 will be described in terms of a clock face, i.e., the positions of the uterine arteries will be identified as corresponding to particular times on a clock. In this context, 12 o'clock is the anterior direction from the center of the cervical os CO, 6 o'clock is posterior therefrom, 3 o'clock is laterally to the right (the patient's left side, see FIG. 2), and 9 o'clock is laterally to the left (the patient's right side, see FIG. 2). As will be readily apparent to those of skill in the art, the use of the clock face as a reference frame is used merely to simplify the discussions herein, and other reference frames, such as degrees or radians from a known or ascertainable reference line, can be interchangeably used herein.

FIGS. 3A and 3B illustrate a first aspect of the present invention which can be useful for occluding a uterine artery. An elongated uterine artery compressor 100 includes a proximal handle portion 102 and a distal compressing portion 104.

The compressor 100 is sized to be insertable through the vagina of a female human patient, along a side of the exterior of the cervix, and to the vaginal wall at the vaginal fornix. The distal compressing portion 104 can be formed with any of numerous shapes to push the vaginal wall at the fornix to invaginate the vaginal wall. By way of example and not of limitation, the portion 104 can be flared outward from the handle 102, as illustrated in FIG. 3A.

Once the compressor 100 has been advanced into the fornix as described above, further pushing of the compressor 100 upwardly toward the uterine artery causes the uterine artery (and adjacent tissues) to be pinched between the distal end 106 of the portion 104 and the uterus itself. As discussed above, the uterus is a firm, muscular organ and therefore acts as a backstop or anvil against which the uterine artery can be compressed. Thus, pushing on the compressor 100 compresses the uterine artery, at least partially, and optionally completely, stopping the blood flow through the artery. As described in the '815 application, cessation of blood flow through the uterine artery can have beneficial effects for the patient.

Figure 8:
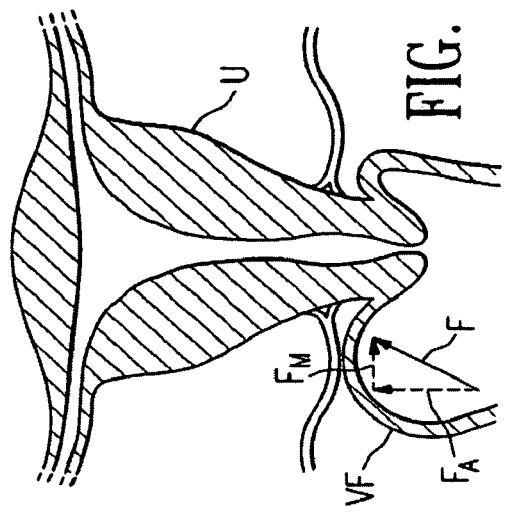
FIG. 8 illustrates a simplified schematic view of a uterus and a force vector.

The direction in which the compression force is applied against the vaginal fornix VF, and therefore against the uterine artery (UA1, UA2), includes at least an axial component $F_A$ (see FIG. 8). According to other aspects of the present invention, the force vector of the force which generates the compression of the uterine artery can include a medial component $F_M$, i.e., the compression force vector F is also directed inward toward the centerline of the uterus U. According to yet further aspects of the present invention, the force vector F can be built by serially applying: an axial force $F_A$, and then a medial force $F_M$; a medial force $F_M$, and then an axial force $F_A$; or simultaneous combinations of axial $F_A$ and medial $F_M$ forces of various magnitudes. The addition of the medial force $F_M$ component of the force vector F can assist in trapping or pinning the uterine artery against the uterus U when the uterus is used as an 'anvil' against which the uterine artery is compressed. According to the aspect of the invention in which the medial force $F_M$ component of the force vector F is used, at least in part, to compress a uterine artery, the distal end face of the compressor is not necessarily the only structure which transmits the force; other portions of the compressor, in particular the laterally facing surfaces of the compressor, also can transmit some of the force F.

FIGS. 4A and 4B illustrate another aspect of the present invention. An elongated uterine artery compressor 150 is somewhat similar to the compressor 100, described above with reference to FIGS. 3A and 3B. The compressor 150 includes a proximal handle portion 152 and a distal compressing portion 154. The compressor 150 is sized to be insertable through the vagina of a female human patient, along a side of the exterior of the cervix, and to the vaginal wall at the vaginal fornix. As can be better visualized in FIG. 4B, at least a portion, and optionally all of the compressing portion 154 has a curved cross-sectional profile. As suggested by the radius R, the curve of the portion 154 can be semi-circular, but in general the curve is selected so that it approximates the shape of the exterior surface of the cervix at least where the cervix meets the vaginal fornix. By forming at least a portion of compressing portion 154 with a concave inner surface 156 which is similar in its curvature to the shape of the exterior surface of the cervix, the cervix itself can be used as a guide toward the uterine artery or arteries. That is, the compressing portion 154 can be pushed along the exterior of the cervix toward the uterine artery with the interior surface 156 riding along the exterior of the cervix. In this manner, the orientation of the compressor 150 relative to the cervix and the uterine artery can be correctly maintained because the cervix acts as a rail on which the compressor rides toward the uterine artery. In a manner similar to that described above concerning compressor 100, the compressor 150 is pushed further up to distend the vaginal wall, press against the uterine artery, and compress the artery against the uterus.

By way of example and not of limitation, a compressor useful for bilaterally compressing the uterine arteries of a female human patient has a hollow interior space which is generally cylindrical with a inner radius between about 1 cm and about 2 cm, preferably about 1.5 cm, an outer radius between about 1.5 cm and about 2.5 cm, preferably about 2 cm, i.e., the wall thickness of the distal end of the compressor is about 0.5 cm or less, and the distal compressing portion is about 1.0 cm or less long longitudinally. These dimensions, and in particular the inner dimension of the distal compressing portion, have been found to be similar in size to the exterior of the cervix of adult female human patients.

FIGS. 5A, 5B, and 5C illustrate yet further aspects of the present invention. FIG. 5A illustrates a front elevational view of an embodiment of a uterine artery compressor 200 which can be used to simultaneously compress both uterine arteries of a female human patient. FIG. 5B illustrates the compressor 200 as viewed from line 5-5 in FIG. 5A, while FIG. 5C illustrates a side elevational view of the compressor. A bilateral compressor in accordance with the present invention, including the compressor 200, is generally a bilateral version of one of the compressors 100, 150, that is, the compressor 200 includes structures similar to the structures described above, but with two sets of the structures arranged in a mirror-image fashion. While including the somewhat cylindrical shape illustrated in FIGS. 5A-5C, bilateral compressors of the present invention include compressors which are shaped like a tuning fork, e.g., two generally parallel, spaced-apart members to which a handle is attached for applying a force to uterine arteries.

Turning back to the exemplary embodiment illustrated in FIGS. 5A-5C, the compressor 200 includes a proximal handle 202 and a distal compressor portion 204. The compressor portion 204 is generally shaped as a hollow cylinder or tube with a hollow interior space 216 which is sized so that the portion 204 can slide over the cervix of the female human patient with little clearance between the interior surface 214 of the compressor portion 204 and the exterior of the cervix. Stated somewhat differently, the distal compressor portion 204 is sized and shaped to receive the cervix in its hollow interior and use the cervix as a rail to guide the portion 204 to the uterine arteries.

The distal compressor portion 204 includes right 206 and left 208 distal ends which engage the vaginal wall VW at the vaginal fornix VF on opposite lateral sides of the cervix when the compressor is pushed up the outside of the cervix. Optionally, the distal compressor portion 204 includes one, and preferably two, cutout portions 210, 212 between the distal ends 206, 208. The cutout portions 210, 212 can be optionally provided in the compressor 200 to accommodate the urethra and bladder neck on the anterior side of the cervix, and the rectum on the posterior side of the cervix. That is, the cutouts 210, 212 are sized, both in their circumferential length and their longitudinal depth, so that when the compressor 200 is used to compress the left and right uterine arteries of a female human patient, the urethra, bladder neck, and rectum are not compressed as much, or are not compressed at all, which can limit or eliminate complications with these structures. Further optionally, one of the cutouts 210 can be formed as a longitudinally extending slot 210' which extends completely along the length of the compressor portion 204, which permits the compressor 200 to be more easily used with other devices, described in greater detail below.

The use of the compressor 200 is similar to the uses of compressors 100 and 150, described above, except that the bilateral structures of the compressor 200 permit both the left and the right uterine arteries UA1, UA2 to be compressed at the same time upon upward pushing of the compressor, and using the body of the uterus as an anvil against which to compress the arteries.

FIG. 6 illustrates yet further aspects of the present invention. FIG. 6 illustrates a front elevational view of a compressor 250 which is similar in many respects to compressor 200, except that compressor 250 includes structures which permit the two sides, left and right, to be moved independently. These additional structures permits the compressor 250 to be used to simultaneously compress uterine arteries which are different distances from the vaginal fornix VF, discussed above. These additional structures also permit the compressor 250 to be used to serially compress the left and right uterine arteries by selectively moving the left and right halves of the compressor 250, respectively.

Turning back to FIG. 6, the compressor 250 includes a proximal handle 252, a distal compressing portion 254, a pair of distal end faces 256, 258, and an optional set of cutouts 260, 262, and an interior wall 264 which delimits an interior space 266, all of which are similar to structures in compressor 200. In addition, the compressor 250 includes a pair of longitudinally extending slots 268, 270 which extend through the distal compressor portion 254, and a longitudinally extending slidable joint 272 formed in the proximal handle 252. The slots 268, 270 and the joint 272 together divide the compressor 250 into a left half 274 and a right half 276, which are longitudinally slidable relative to each other. In order to permit the two halves 274, 276 to resist relative longitudinal motion, a lock can optionally be further provided which secures the two halves together. By way of example and not of limitation, the slidable joint 272 can be formed as a tongue and groove type joint with the faces of the joint formed of a material or of materials which require a relatively high force to overcome the friction between the faces of the joint. Other locking mechanisms within the scope of the present invention include, but are not limited to, spring clips and clamps which clamp the two halves of the handle together, and the like.

Figure 7C:
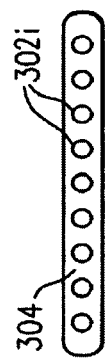
FIGS. 7A, 7B, and 7C illustrate three views of yet another embodiment.
Figure 7B:
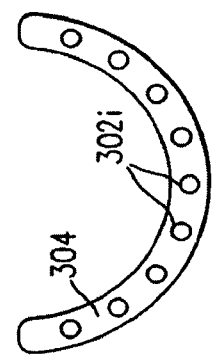
Figure 7A:
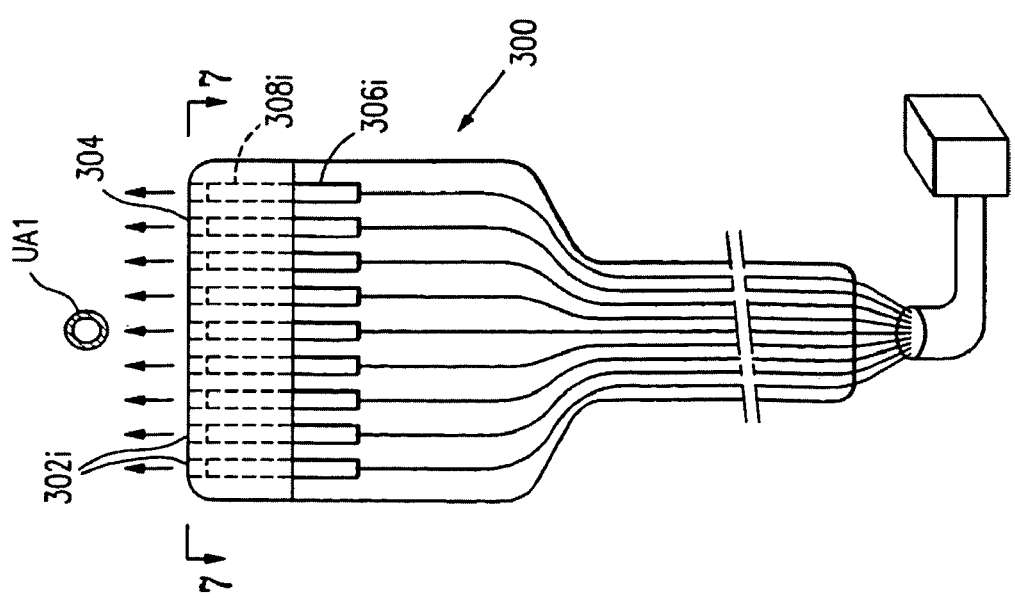

FIGS. 7A-7C illustrate yet further aspects of the present invention. FIG. 7A illustrates the distal end of a portion of a bilateral compressor, or the distal end of a unilateral compressor, 300. The compressor 300 can be any of the compressors described herein, and therefore further descriptions of the features of the compressor will not be given here. The compressor 300 includes at least one, and particularly advantageously a plurality of Doppler ultrasound crystals 302i oriented with the viewing direction of the crystals pointed distally, as suggested by the arrows in the drawing figure. While a plurality of crystals 302i can be advantageous in providing more data about the flow of blood through the uterine artery of interest, the additional data requires additional manipulation that can increase the complexity and cost of the device. Thus, it may in some circumstances be advantageous to provide fewer, or only a single, crystal 302i, to reduce the complexity of the Doppler data that must be interpreted.

The crystals 302i are preferably positioned at the distal face 304 of the compressor so that any data derived from the signals received by the Doppler crystals can be more easily correlated to the distance of the uterine artery from the distal end 304. The crystals 302i can be integrated into the compressor 300, e.g., molded into the compressor itself, or alternatively can be removably mounted in the compressor. By way of example and not of limitation, the Doppler crystals 302i can each be in a Doppler probe 306i which is received in a correspondingly configured holder 308i formed in distal portions of the compressor. While many commercially available Doppler probes are suitable in the present invention, a Vascular Technology, Inc. (Lowell, Mass.) 8 MHz Doppler probe, or a Koven 8 MHz Doppler probe (Koven, St. Louis, Mo.), can be used as a Doppler probe 306i.

Those of skill in the art will recognize that the frequency of the Doppler crystal will change the viewing angle of the crystal. One aspect of the present invention is the use of Doppler crystals 302i which permit Doppler data to be gathered at distances up to about 3 cm, so that when the compressor on which the Doppler crystals are mounted is pushed against the vaginal wall at the vaginal fornix VF, the Doppler crystals 302i will received signals back from the uterine artery of interest. Thus, while many different Doppler crystals are suitable in the present invention, those which operate at about 8 MHz have been found to be particularly suitable.

The signals from the Doppler crystals 302i or probes 306i are transmitted to a suitable signal processor which displays data derived from the signals. According to yet further aspects of the present invention, the data from each of the Doppler crystals 302i is either manually or automatically examined to ascertain if the waveform received by the crystal is representative of the blood flow through a uterine artery UA1. Because the Doppler crystals 302i are selected to have relatively narrow angles of view, the process of examining the signals received by each crystal will reveal which crystal is pointed most directly at the uterine artery. As illustrated in FIGS. 7B and 7C, the compressor 300 can be curved or relatively flat. In the embodiments in which the compressor is curved with an interior surface which is generally complementary to the exterior surface of the cervix, the identification of the crystal 302i which is most pointed at the uterine artery UA1 also gives the relative angular position of the uterine artery, e.g., at the 3 o'clock position. Because the inventors herein have discovered that uterine arteries in female humans are positioned between certain clock positions (angular positions), it is not necessary to equip the compressors of the present invention with Doppler crystals so as to cover 180 degrees (unilateral) or 360 degrees (bilateral). Other aspects of the present invention, however, include providing Doppler crystals on compressors so that the entire 360 degrees around the cervix can be easily sampled, for example to accommodate the positions of statistically less likely positions of uterine arteries.

Figure 9B:
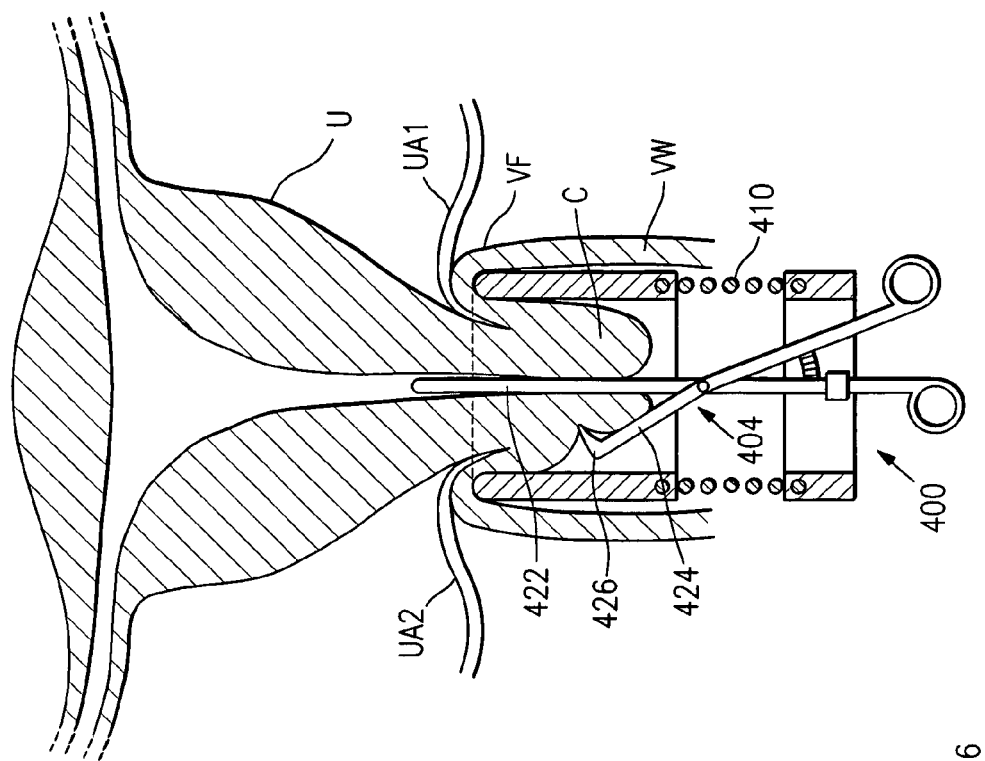
FIGS. 9A, 9B, and 9C illustrate yet other embodiments in accordance with the present invention, which includes a position holding device.
Figure 9A:
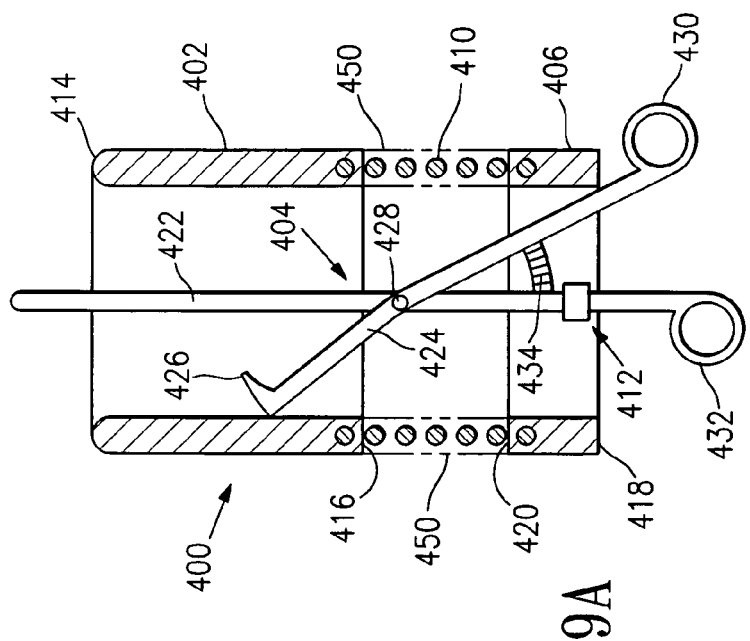

FIGS. 9A and 9B schematically illustrate further aspects of the present invention. FIG. 9A illustrates a cross-sectional view of a compressor 400 in accordance with yet another embodiment of the present invention. The compressor 400 includes structures which allow the compressor to compress the uterine arteries UA1, UA2 with a constant force while securing itself to the patient. These additional functions relieve the practitioner from having to hold onto the compressor while compressing the uterine arteries. As will be readily appreciated by those of skill in the art, other aspects of the present invention include that these structures are incorporated into the other embodiments disclosed herein.

Turning now to the drawing figures, the compressor 400 includes a distal compressing portion 402, which can take the form of any of the other compressing portions described herein (e.g., 100, 150, 200, 250, 300), a tenaculum-like grasping device 404, and a force transmission block 406. A constant force generating member 410 is mounted between the proximal end 416 of the compressing portion 402 and the distal end 420 of the block 406. An example of a constant force generating member 410 is a constant force helical spring. The compressing portion 402 includes a distal compressing face 414, and the block includes a proximal end 418.

The compressing portion 402 illustrated in FIG. 9A is generally tubular, in a manner similar to other compressing portions described herein. Another aspect of the present invention includes that the compressing portion 402 is shaped such as compressing portion 154 (see FIG. 4A), e.g., semicircular or other open curved shape including a concave interior surface. According to this aspect of the present invention, the constant force generating member 410 is attached to corresponding proximal portions of the compressing portion.

A holding element 412 is provided on the block 406 for holding the grasping device 404 securely to the block and against relative longitudinal movement between the two structures. The holding element 412 can either removably or permanently hold the grasping device to the block 406. By way of example and not of limitation, a removable holding element 412 can include a hinged snap which traps a portion of the grasping device between two jaws, while a permanent holding element 412 can include the grasping device being molded into the block.

The grasping element includes a longitudinally extending first element 422, a second angled element 424, and a hinge or pivot 428 connecting the first and second elements together. The second element 424 includes an inwardly directed grasping portion 426, which can have a claw-like shape to grasp tissue between the grasping portion and the first element 422. A ratcheting lock 434 releasably holds together proximal portions of the first element 422 and the second element 424, as are well known to those of skill in the art. The proximal ends of the first element 422 and the second element 424 can include finger rings 432, 430, respectively.

FIG. 9B illustrates an exemplary use of the compressor 400 in accordance with the present invention. The compressor 400 can be provided with Doppler elements as described herein which generate signals which are indicative of blood flow through the uterine arteries UA1, UA2, or the additional functionality of these elements can optionally not be included. As the use of the Doppler elements is described elsewhere herein, reference here is only made to those portions of this disclosure and will not be repeated.

The grasping device 404 is positioned with the first element 422 in the cervical canal and the second element 424 outside of the cervix C. The grasping device is then manipulated to push the grasping portion 426 medially into the cervix C to grasp the tissue of the cervix, while the ratcheting lock 434 holds the first and second elements 422, 424 in their relative angular orientation. For those embodiments of the present invention in which the holding element 412 releasably holds the proximal portions of the grasping device 404, the compressing portion 402 is slipped over the grasping device 404 and pushed up against the vaginal wall at the vaginal fornix, compressing the uterine arteries UA1, UA2. The holding element 412 is then secured to the grasping device 404 to hold the compressing portion 402 in place, while the constant force element 410 exerts a constant force on the compressing portion, and therefore on the uterine arteries UA1, UA2.

For those embodiments of the present invention in which the holding element 412 permanently holds the proximal portions of the grasping device 404, the compressing portion 402 is pushed over the outer surface of the cervix C at the time that the first element 422 is pushed into the cervical canal.

With the grasping device 404 holding the cervix C and the block 406 secured to the grasping device, the constant force element 410 pushes with a constant force on the compressing portion 402 in at least a distal, longitudinal direction.

Yet a further aspect of the present invention, as described above, is the addition of a medially directed force. According to yet another embodiment of the present invention, the compressing portion 402 is formed as a frustocone, and the block 406 is formed to have a larger transverse size at it's distal end 420 that the transverse size of the proximal end 416 of the compressing portion. In this manner, the constant force element 410 also takes the shape of a frustocone, and the force generated by the element 410 includes both longitudinal and medial components.

Yet another aspect of the present invention is that, as discussed above, the compressing portion 402 can be shaped more like compressing portion 154, that is, is not tubular as illustrated in FIGS. 9A and 9B, but is more C-shaped. When in this configuration, the compressing portion proximal end 416 is laterally spaced from the grasping device 404 a distance less that the force transmission block distal end 420 is laterally spaced from the grasping device.

Yet further optionally, the cervix C can be pulled by the grasping device 404, and more particularly by the claw 426, prior to securing the compressing portion 402 to the grasping device.

Yet further aspects of the present invention exclude the constant force generating element 410, and the compressing portion and the force transmission block are directly connected together. While eliminating the functions provided by the constant force generating member 410, the resulting compressor is simpler in construction, and easier and less costly to manufacture. This aspect is the present invention is suggested by phantom line 450.

Figure 10A:
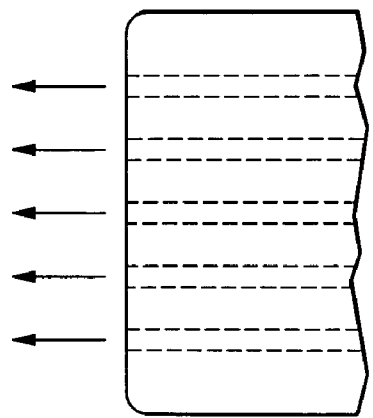
FIGS. 10A, 10B, and 10C schematically illustrate side elevational views of yet other embodiments in accordance with the present invention.
Figure 10B:
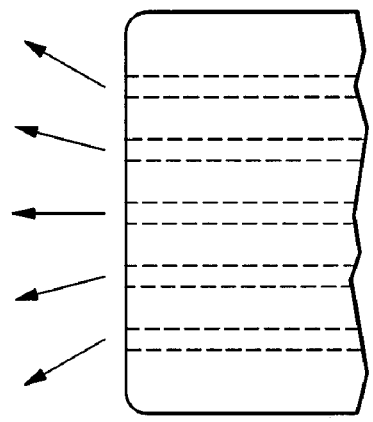
Figure 10C:
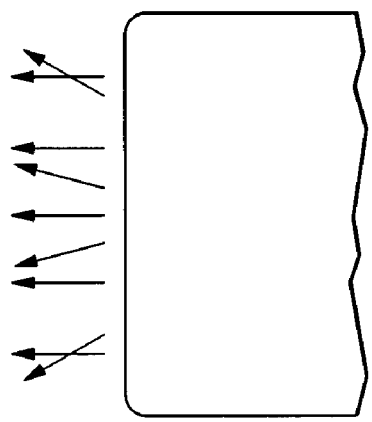

FIGS. 10A-10C illustrate yet further aspects of the present invention. More specifically, the directions of view of the Doppler crystals can be substantially parallel (FIG. 10A), divergent or convergent (FIG. 10B), or combinations of parallel and di-/convergent directions of view.

Figure 9C:
Figure 11C:
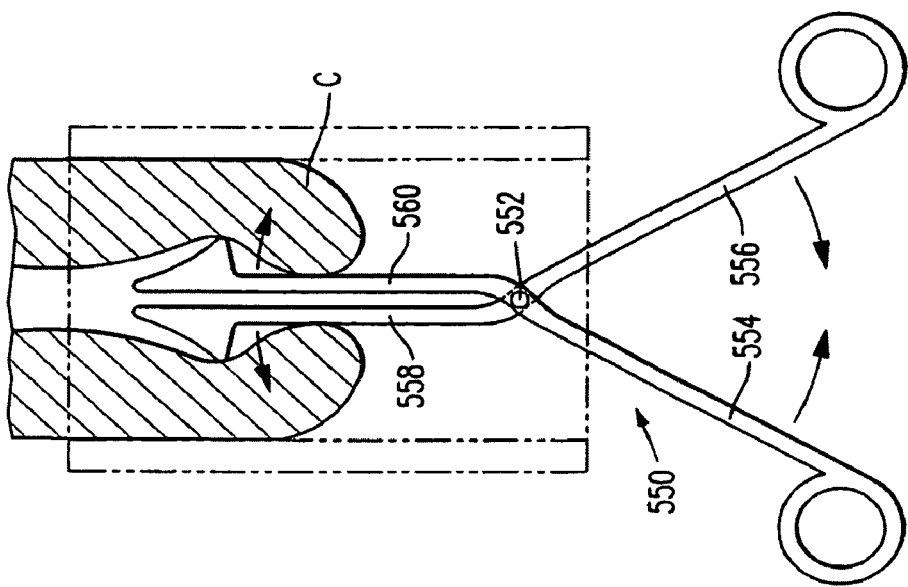
FIGS. 11A, 11B, 11C, 11D, 11E, and 11F illustrate yet further embodiments of devices in accordance with the present invention.
Figure 11B:
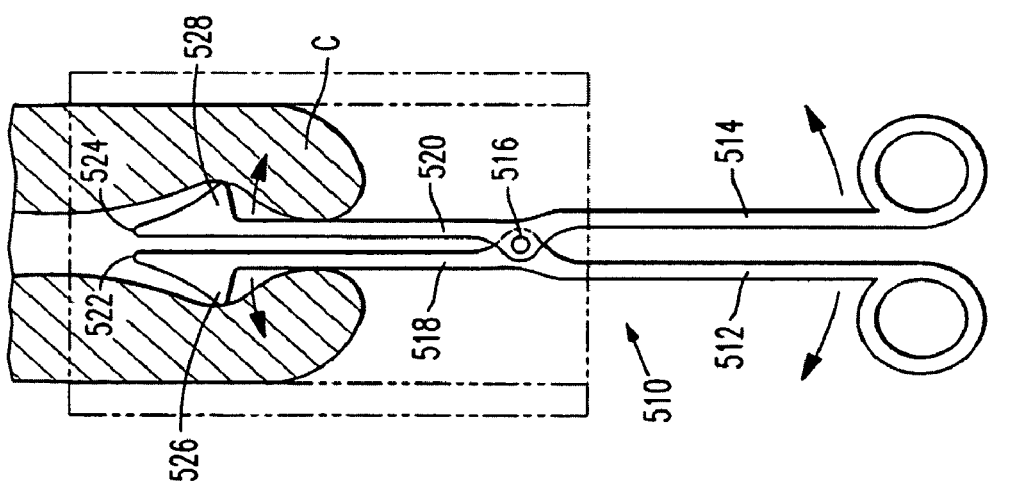
Figure 11A:
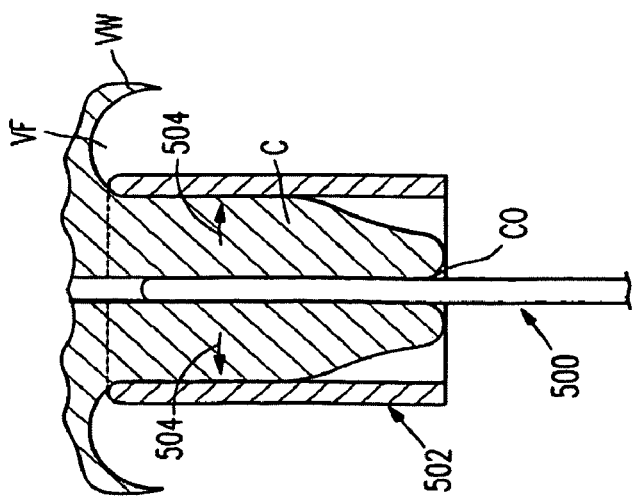

FIGS. 11A-11E illustrate further aspects of the present invention. FIG. 11A illustrates the vaginal wall VW, fornix VF, cervix C, and cervical OS CO of a female patient in a manner similar to other illustrations herein. A compressor 502 is positioned adjacent to the exterior of the cervix C; the compressor can be any of the compressors in accordance with the invention. A device 500 is illustrated in a position inserted into the cervical os CO and cervix C. As illustrated generally with the laterally extending arrows 504, the device 500 includes structures which push the cervix laterally outward and press the cervix against the inner surface of the compressor 502. While FIG. 11A illustrates that the device 500 pushes the cervix C multilaterally, e.g., bilaterally, another aspect of the invention is that the device pushes only in one direction. The force of the device 500 presses the cervix C against the compressor 502, and holds the compressor in place. Therefore, when a compressor 502 is used in accordance with the invention to compress a uterine artery, the device 500 can be used to hold the compressor to the cervix for a desired period of time, e.g., a therapeutically effective period of time. Optionally, the device 500 can include structures which releasably hold the device to the compressor, an example of which can be formed like the force transmission block 412 described with reference to FIGS. 9A-9C. In general terms, the device 500 functions at least to outwardly push or dilate at least a portion of the cervix, and therefore the device 500 will be referred to as a dilator.

FIG. 11B illustrates an embodiment of a dilator useful for insertion into the cervix C to hold a compressor in place to compress a uterine artery. The dilator 510 includes a first handle 512 and a second handle 514. The first and second handles 512, 514 are connected together at a pivot or hinge 516. Distally of the pivot 516, a pair of arms 518, 520 are attached to the handles 512, 514, respectively. Notably, the arms are connected to the handles so that the two arm-handle combinations are on opposite lateral sides of the pivot 516. The arms 518, 520 have distal ends 522, 524, which are preferably rounded so that the dilator 510 can be atraumatically inserted into the cervix C. According to a preferred embodiment, at least one, and preferably both of the arms include a grasping portion 526, 528, which protrudes laterally away from the arm. The grasping portions 526, 528 can assist in holding the dilator 510 to the cervix C, and can assist in pinching the cervix between the dilator and the compressor to hold the compressor in place. According to the exemplary embodiment illustrated in the drawing figures, the grasping portions 526, 528 can be pointed, thorn or spike shaped elements which extend laterally outwardly from the arm.

In the embodiment illustrated in FIG. 11B, each of the arm-handle combinations extend along only one side of the pivot 516, i.e., the two arm-handle combinations do not cross. Because of this orientation of the structures, and as suggested by the arrows in FIG. 11B, pulling apart the two handles 512, 514 results in the two arms 518, 520 moving laterally outwardly and away from each other. When the dilator 510 is used in situ in the cervix C, moving the handles 512, 514 outwardly results in the arms 518, 520 expanding and dilating the cervix. When the arms 518, 520 are provided with the optional grasping portions, the cervix C can be more effectively pinched between the dilator 510 and the compressor 502.

As further option, a releasable lock (not illustrated) may be included which releasably locks together the handles 512, 514, so that the dilator 510 can be released by the practitioner while maintaining the positions of the arms 518, 520 relative to one another.

Turning now to FIG. 11C, yet another embodiment 550 of a dilator 500 is illustrated. The dilator 550 is similar in construction to the dilator 510, and therefore only the differences will be described. As illustrated in FIG. 11C, the handles 554, 556 are both connected to distal arms 560, 558, but the arm-handle combinations cross over at the pivot 552. Additionally, each of the handles 554, 556 are preferably formed at an angle to the arms 560, 558, so that the handles can more easily be pressed laterally together to expand the arms and dilate the cervix C, as suggested by the arrows in the drawing figure.

Figure 11F:
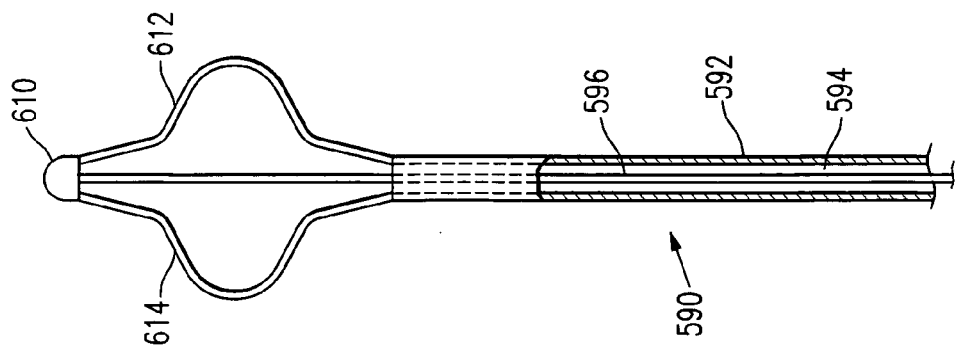
Figure 11E:
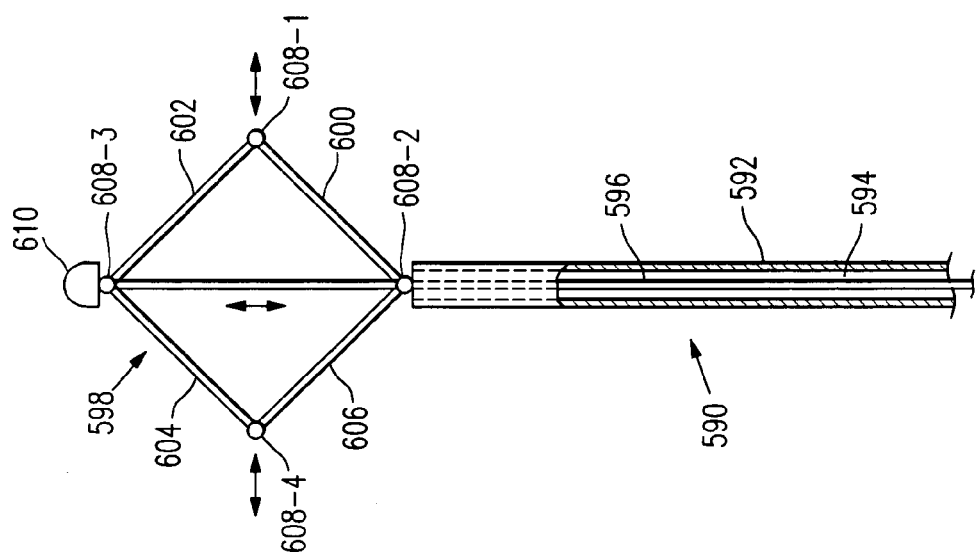
Figure 11D:
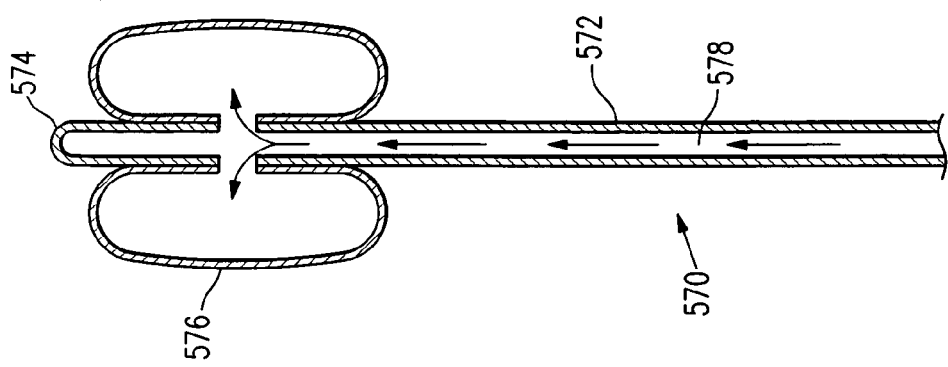

FIG. 11D illustrates yet another embodiment 570 of the dilator 500. The dilator 570 includes a relatively rigid cannula 572 having a longitudinally extending lumen 578. One or more inflatable members 576, e.g., balloons, are mounted on the cannula 572 and are in fluid communication with the lumen 578. The distal end 574 of the cannula 572 is preferably rounded to be atraumatic when inserted into the cervix. While it is within the scope of the present invention for the inflatable member(s) 576 to occupy the entire circumference of the cannula 572, it can be sufficient for there to be only a single inflatable member. Furthermore, it can be sufficient for the single inflatable member 576 to occupy less than the entire circumference of the cannula. As will be readily appreciated by those of skill in the art, inflation of the inflatable members(s) with an inflation fluid causes the inflatable members to expand, thereby pushing the cervix outward and holding it against the compressor.

FIG. 11E illustrates yet another embodiment 590 of the dilator 500. The dilator 590 includes a relatively rigid cannula 592 having a longitudinally extending lumen 594. A push-pull rod 596 extends from the proximal end of the dilator (not illustrated) to the distal tip 610, which is preferably rounded to be atraumatic for insertion into the cervix. Proximal of the distal tip 610 is positioned an expansion member 598, e.g., an expandable cage. According to the exemplary embodiment illustrated in FIG. 11E, the expansion member 598 includes at least two arms 600, 602, joined together at a pivot or hinge 608-1. The arm 600 is attached to the cannula 594 at a pivot or hinge 608-2, and the arm 602 is attached to the distal tip 610 at a pivot or hinge 608-3. Preferably, the expansion member 598 includes a plurality of expanding linked arms, such as arms 600, 602, an example of which is illuatrated by arms 604 and 606, joined together at pivot 608-4. As suggested by the arrows in FIG. 11E, proximal movement of the rod 596 pulls the distal tip 610 proximally, which pushes the arms (e.g., arms 600, 602) outwardly against the cervix. As the rod 596 is pulled proximally, the cervix is dilated and pinched against the compressor, which can hold the compressor in place.

Further optionally, the pivot points 608 can be formed integrally with the arms, either as a living hinge, or the arms themselves, e.g., arms 600 and 602, are formed as a single bow or malecot 612, 614 (see FIG. 11F) which is naturally curved outwardly. As such structures are themselves well known to those of skill in the art, they will not be described herein. Examples of such structures are described in U.S. Pat. Nos. 3,108,595 and 4,995,868.

Another aspect of the present invention relates to further processes of treatment of a patient, e.g., using a compressor. Once it has been established that the blood flow through the uterine artery or arteries has stopped for a therapeutically effective period of time, the practitioner can release the compressing member from compressing the uterine artery, and remove the compressing member from the patient. In the context of compressor 400, for example, the practitioner releases the ratchet lock and retracts the compressor 400 from along the cervix of the patient. This removal step can also be performed for any of the devices, and in combination with any of the methods, described herein. As used herein, the term therapeutically effective time and its equivalents are used as in U.S. patent application Ser. No. 09/556,934, filed Apr. 21, 2000, by Burbank et al., now U.S. Pat. No. 6,550,482, and U.S. patent application Ser. No. 09/908,815, filed Jul. 20, 2001, by Burbank et al.,now U.S. Pat No 7,223,279, the entireties of both of which are incorporated herein by reference.

According to a particularly preferred embodiment of the present invention, the hollow interior space of the cylindrical compressing portion has an inner diameter between about 2 cm and about 4 cm, and more preferably about 3 cm, because this size matches well the outer diameter or size of the cervix of many females. As will be well appreciated by those of ordinary skill in the art, the size of the hollow interior space can be larger or smaller according to the present invention, to fit a larger or smaller cervix.

Another aspect of the present invention includes that one or more of the surface(s) of the compressor, including each of the compressors described herein, which bears against the outer surface of the cervix can be formed as a generally flat surface instead of a concave surface.

The present invention also relates to devices, systems, and processes which can be useful in treating dysfunctional uterine bleeding (DUB). As the skilled artisan readily appreciates, DUB can be a very frustrating and troublesome condition because the actual cause of the bleeding is, by definition, unknown. Stated somewhat differently, DUB is a diagnosis of exclusion; if a woman has menorrhagia and no organic abnormality can be identified, she is given the diagnosis of DUB. Women with DUB are debilitated just as are women with fibroids and menorrhagia: they can be socially restricted during times of high menstrual blood loss and are anemic. Other aspects of the present invention relate to treating a patient who is diagnosed with DUB by compressing one or both uterine arteries, either serially or simultaneously, so that the uterine blood supply is greatly diminished or completely cut off. Without the blood supplied by the uterine arteries, the uterus stops bleeding, which can permit the medical practitioner to better diagnose the patient's condition. Without being limited to a particular theory, it is also posited herein that at least some cases of DUB can be treated effectively by uterine artery compression as described herein, that is, that DUB will not reoccur upon reestablishment of the blood supply to the uterus through the uterine arteries. To put it somewhat colloquially, the apparatus and methods of the present invention can be used to 'reset' the uterus by going through a period of induced anoxia or hypoxia. The Bateman article, mentioned briefly above, lends support to this hypothesis.

The present invention also includes as an aspect the treatment of bleeding associated with Caesarian section. Caesarian delivery results in at least two sources of post partum bleeding: blood loss at the Caesarian incision site; and blood loss at the placental separation site. Generally, natural mechanisms control blood loss at the placental separation site, while blood loss at the Caesarian incision site is typically achieved by suturing the two margins of the incision firmly together. The pressure of the sutures slows blood flow at the incision site and clot then forms; however, until sufficient suturing has been accomplished, blood loss occurs. Because suturing the Caesarian incision site is performed under urgent circumstances, to minimize blood loss, suturing quality of the incision is performed as if the uterus were composed of one layer of tissue, instead of three. Consequently, the outcome of this prior method is suboptimal at the endometrial, myometrial, and serosal levels. Thus another aspect of the present invention is the use of devices and/or the performance of methods in accordance with the present invention instead of, or in conjunction with, these prior suturing methods to treat Caesarian delivery bleeding. More specifically, devices and/or methods of the present invention re used and/or implemented to slow or stop blood flow to the uterus through the uterine arteries immediately after a baby is delivered. Subsequently, Caesarian incision repair can be performed in a manner that optimizes surgical closure, without worry about blood loss control at the time of closure.

The present invention also includes as an aspect the treatment of bleeding associated with Post Partum Hemorrhage (PPH). PPH is defined in the medical literature as the estimated loss of more than 500 ml of blood following delivery of a baby. It can occur for a wide variety of reasons and occurs following at least 5% of deliveries. Most often it occurs because the uterus fails to contract following placental separation (uterine atony). Without adequate post partum uterine contractions, blood does not slow enough in the uretoplacental arteries to clot. Without clot formation in the uretoplacental arteries, bleeding from the uretoplacental arteries persists.

Many treatments exist for hemorrhage secondary to uterine atony, including massage of the uterus through the abdominal wall, administration of drugs that encourage myometrial contraction (e.g., oxytocin, methylergonovine, and prostaglandins), uterine cavity packing with, e.g., cloth materials, balloon tamponade of the uterine cavity, bilateral surgical ligation of the uterine artery, ovarian arteries, or internal iliac artery, bilateral uterine artery embolization, suturing through the uterus (e.g., B-Lynch Brace technique), and hysterectomy. Many of the existing treatments are ineffective; others are overly complex, invasive, and slow to initiate.

According to aspects of the present invention, when it is recognized that bleeding has not stopped normally as it should after delivery, devices and/or methods in accordance with the present invention can be employed as described herein to slow or stop PPH.

The present invention extends at least to include devices and methods including combinations of all of the features and steps described above. By way of example and not of limitation, the Doppler probe array(s) described herein can be incorporated into any of the exemplary devices described herein, arranged at the distal end(s) of the device(s) as will be readily apparent to one of skill in the art. In a similar manner, methods of the present invention can include, but are not limited to, any one or combinations of the steps described above. Furthermore, any of the above described devices and methods which are described as useful for occluding a single uterine artery can be incorporated into bilateral devices and methods, that is, two of the unilateral devices can be joined into a single, bilateral device, with each of the two unilateral devices positioned in the bilateral device to access and/or locate a single uterine artery, and the steps of a method for accessing and/or locating a single uterine artery can be performed bilaterally, either serially or simultaneously.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. An intravaginal device for occluding a uterine artery of a female patient having a uterus, a uterine cervix, a vaginal canal leading to the uterine cervix and a vaginal fornix surrounding the uterine cervix, comprising:
    a first pressure applying arcuate member having a distal pressure applying end configured to invaginate tissue of the patient's vaginal fornix and to occlude an underlying uterine artery and an arcuate concave side surface proximal to the distal pressure applying end configured to conform to an exterior side portion of the patient's cervix;
    a second pressure applying member having a distal pressure applying end and an arcuate concave side surface configured to conform to an exterior side portion of the patient's cervix spaced apart from the first pressure applying member, wherein at least one of the first and second pressure applying members has at least one Doppler crystal mounted therein; and
    an elongated handle secured to the first pressure applying member and having a proximal end configured to extend out of the patient's vagina when the first pressure applying end is pressed against the patient's vaginal fornix.

2. A device in accordance with claim 1, wherein the at least one Doppler crystal is releasably mounted in the distal end of the first or second pressure applying members.

3. A device in accordance with claim 1, wherein the at least one Doppler crystal is integrally formed in the distal end of the first or second pressure applying members.

4. A device in accordance with claim 1, wherein a plurality of Doppler crystals are mounted in the distal end of the first or second pressure applying members.

5. A device in accordance with claim 4, wherein at least two of the Doppler crystals have parallel views.

6. A device in accordance with claim 4, wherein the Doppler crystals each have a direction of view perpendicular to the arcuate side surface.

7. A device in accordance with claim 4, wherein at least two of the Doppler crystals have diverging directions of view.

8. A device in accordance with claim 4, wherein a first plurality of Doppler crystals have a first direction of view, and a second plurality of Doppler crystals have a second direction of view at an angle to the first direction of view.

9. A device in accordance with claim 4, wherein the Doppler crystals are releasably mounted.

10. A device in accordance with claim 4, wherein at least one Doppler crystal is integrally formed in the arcuate side surface.

11. A device in accordance with claim 4, wherein a plurality of Doppler crystals are equally spaced from each other.

12. The device in accordance with claim 1 wherein the first and second pressure applying members are secured together.

13. The device in accordance with claim 12 wherein the first and second pressure applying members are secured together by a support structure which is configured to encircle the patient's uterine cervix.

14. The device in accordance with claim 1 wherein the at least one Doppler crystal comprises a Doppler crystal mounted in the first pressure applying member having a direction of view extending distally away from the distal end of the first pressure applying member.

15. An intravaginal device for at least partially occluding a uterine artery of a female patient having a uterus, a uterine cervix, a vaginal canal leading to the uterine cervix and a vaginal fornix surrounding the uterine cervix, comprising:
 a cylindrical member having at least a pair of opposed distal pressure applying end surfaces, and having one or more arcuate side walls proximal to the distal pressure applying end surfaces with a concave surface defining in part a hollow interior configured to receive the uterine cervix of the female human patient therein when the pressure applying end surfaces are positioned against the vaginal fornix of the female human patient to occlude the patient's underlying uterine arteries, wherein at least one of the pressure applying end surfaces of the cylindrical member has at least one Doppler crystal mounted therein; and
 an elongated handle secured to the cylindrical member and having a proximal end which extends out of the patient's vaginal canal for manipulation.

16. A device in accordance with claim 15, wherein the hollow interior of the cylindrical member has an inner diameter between about 2 cm and about 4 cm.

17. A device in accordance with claim 15, wherein the hollow interior of the cylindrical member has an inner diameter of about 3 cm.

18. A device in accordance with claim 15, wherein the at least one Doppler crystal is releasably mounted in one of the distal pressure applying end surfaces.

19. A device in accordance with claim 15, wherein the at least one Doppler crystal is integrally formed in one of the distal pressure applying end surfaces.

20. A device in accordance with claim 15, wherein the at least one Doppler crystal comprises a plurality of Doppler crystals mounted in the one of the distal pressure applying end surfaces.

21. A device in accordance with claim 20, wherein at least two of the Doppler crystals have parallel views.

22. A device in accordance with claim 20, wherein at least two of the Doppler crystals have views perpendicular to an interior surface of the cylindrical member.

23. A device in accordance with claim 20, wherein at least two of the Doppler crystals have diverging views.

24. A device in accordance with claim 20, wherein a first plurality of Doppler crystals have a first direction of view, and a second plurality of Doppler crystals have a second direction of view at an angle to the first direction of view.

25. A device in accordance with claim 20, wherein the Doppler crystals are integrally formed in the one of the distal pressure applying end surfaces.

26. A device in accordance with claim 20, wherein a plurality of the Doppler crystals are equally spaced from each other.

27. A device in accordance with claim 20, wherein the cylindrical member includes a proximal end, and wherein the cutout comprises a slot extending proximally from the one of the distal pressure applying end surfaces to a proximal portion of the cylindrical member.

28. A device in accordance with claim 15, wherein at least one cutout is provided in one of the distal pressure applying end surfaces of the cylindrical member.

29. A device in accordance with claim 15, wherein the cylindrical member is provided with two cutouts in the distal pressure applying end surfaces thereof.

30. A device in accordance with claim 29, wherein the two cutouts are on diametrically opposite sides of the distal pressure applying end surfaces of the cylindrical member.

31. A device in accordance with claim 29, wherein the cylindrical member includes a proximal end, and further comprising a pair of slots extending proximally from the distal pressure applying end surfaces to the proximal end of the cylindrical member.

32. An intravaginal device for occluding uterine artery comprising:
 a first pressure applying arcuate member having a distal pressure applying end configured to invaginate tissue of a patient's vaginal fornix and to occlude an underlying uterine artery and an arcuate concave side surface proximal to the pressure applying end configured to conform to an exterior side portion of the patient's cervix;
 at least one Doppler crystal mounted on the first pressure applying member; and
 an elongated handle secured to the first pressure applying member and having a proximal end configured to extend out of the patient's vagina when the first pressure applying end is pressed against the patient's vaginal fornix.

33. A device in accordance with claim 32, further comprising:
 a second pressure applying member having a distal pressure applying end and an arcuate concave side surface configured to conform to an exterior side portion of the patient's cervix spaced apart from the first pressure applying member; and
 at least one Doppler crystal mounted on the second pressure applying member.

34. A device in accordance with claim 33, wherein the at least one Doppler crystal is releasably mounted in the distal end of the first or second pressure applying members.

35. A device in accordance with claim 33 wherein the at least one Doppler crystal is integrally formed in the distal end of the first or second pressure applying members.

36. A device in accordance with claim 33, wherein a plurality of Doppler crystals are mounted in the distal end of the first or second pressure applying members.

* * * * *

UNITED STATES PATENT AND TRADEMARK OFFICE
CERTIFICATE OF CORRECTION

PATENT NO. : 7,594,890 B2
APPLICATION NO. : 10/107800
DATED : September 29, 2009
INVENTOR(S) : Burbank et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1068 days.

Signed and Sealed this

Twenty-eighth Day of September, 2010

David J. Kappos
*Director of the United States Patent and Trademark Office*